United States Patent [19]

Bloh

[11] Patent Number: 4,962,189

[45] Date of Patent: Oct. 9, 1990

[54] RIBOTOXIN CONJUGATES

[75] Inventor: Will Bloch, El Cerrito, Calif

[73] Assignee: Cetus Corportion, Emeryville, Calif.

[21] Appl. No.: 131,646

[22] Filed: Dec. 11, 1987

Related U.S. Application Data

[62] Division of Ser. No. 747,114, Jun. 20, 1985, abandoned.

[51] Int. Cl.[5] .................... A61K 37/02; A61K 39/00; C07K 15/28

[52] U.S. Cl. .................................... 530/391; 530/370; 530/377; 530/387; 530/388; 530/390; 530/402; 530/403; 530/404; 530/405; 530/406; 530/408; 530/409; 530/410; 530/411; 424/85.91; 514/885

[58] Field of Search ............... 530/370, 377, 387, 391, 530/402–406, 408–411; 424/85.91; 514/885

[56] References Cited

U.S. PATENT DOCUMENTS 4,771,128 9/1988 Ferris et al. ........................ 530/370

OTHER PUBLICATIONS

Funatsu et al., *Agric. Biol. Chem.* 42, 1978, pp. 851–859.

Mise et al., *Agric. Biol. Chem.* 41(10) 1977, pp. 2041–2046.

Middlebrook et al., *Microbiol. Rev.* 48(3) 1984, pp. 199–221.

Olsnes et al., *Pharma. Ther.* vol. 15, 1982, pp. 355–381.

Appukuttan et al., *Biochimica et Biophysica Acta,* 580: 10–14 (1979).

*Primary Examiner*—Garnette Draper

*Attorney, Agent, or Firm*—Wean K. Wong; Gregory J. Giotta; Albert P. Halluin

[57] ABSTRACT

The invention herein is directed to methods using Procion dyes to perform separations of interest in manipulating the $NAD^+$-independent ribotoxins. The methods are useful for preparing therapeutic agents containing these ribotoxins or their A polypeptide components. This separation method has been applied in particular to preparing hybrid toxins containing ricin toxins, both for purifying the resulting products and also for separating the components intended to be used in the preparation of these end products. In addition, a novel ricin isotoxin prepared using the method of the invention is disclosed.

4 Claims, 11 Drawing Sheets

FIG. 1
Salt-Gradient Fractionation of
RTA Isozymes on Blue Trisacryl M
A. Elution Profile
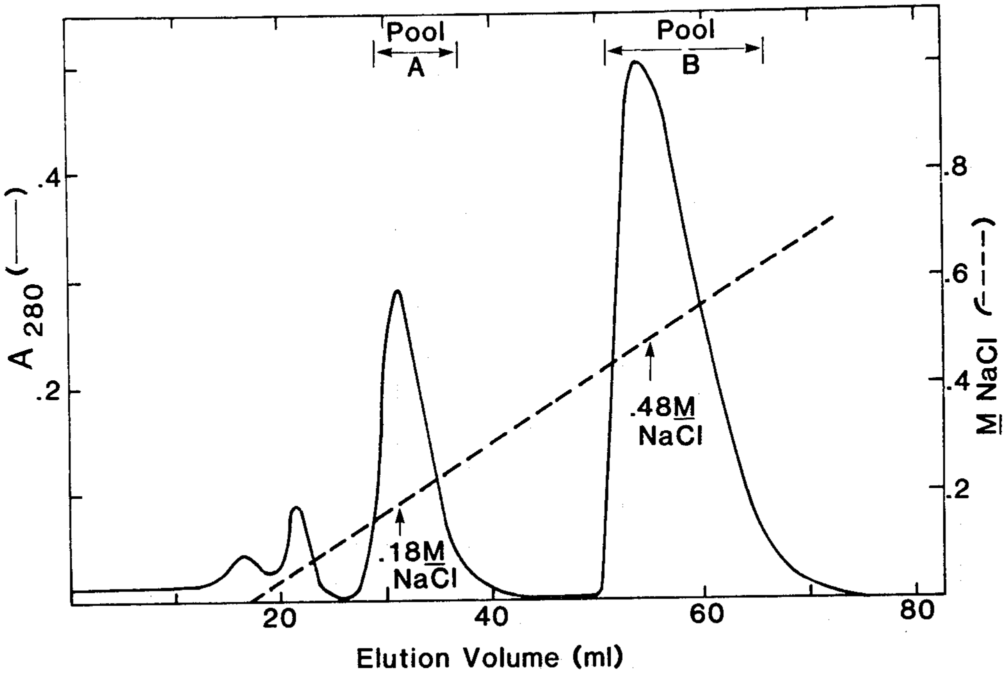
B. Reduced 12.5% SDS-PAGE
| Lane | Sample |
| --- | --- |
| 1 | MW Standards |
| 2 | Unfractionated RTA |
| 3 | Pool A |
| 4 | Pool B |
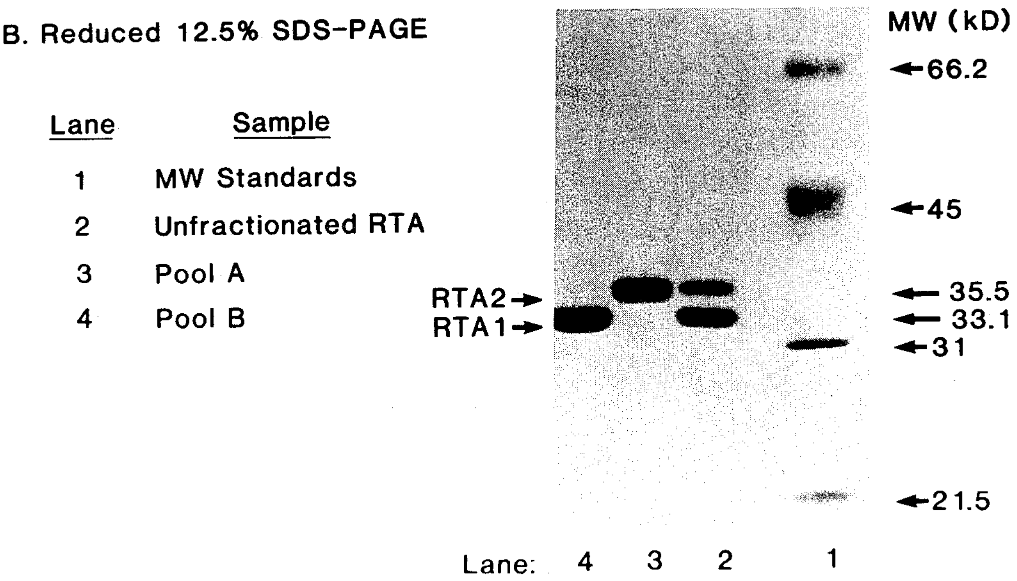

Salt-Gradient Fractionation of Ricins D, E2, and E1 on Blue Trisacryl M

FIG. 3
Resolution of RTB and RTA from Reduced Ricin E1 on Blue Trisacryl M
A. Elution Profile
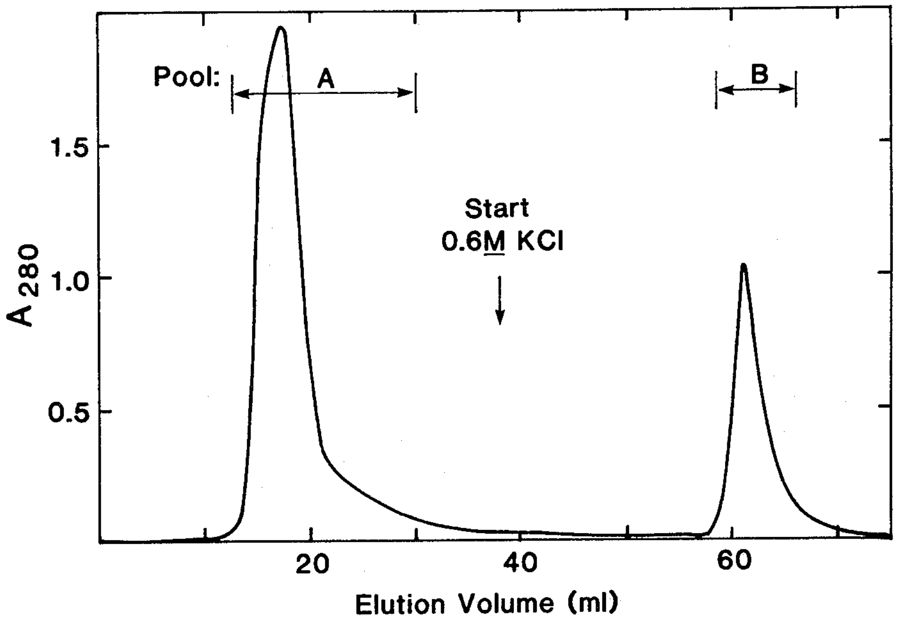
B. Isoelectric Focusing of Chromatographic Pools
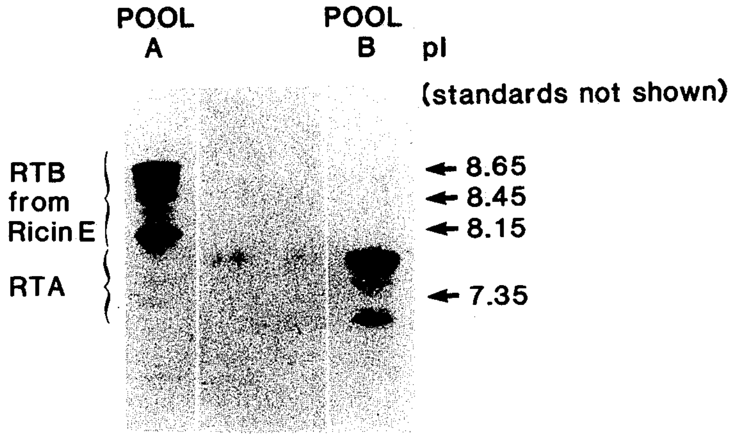

FIG. 4

Fractionation of the Coupling Reaction Mixture for Ricin A Chain-IgG Immunoconjugate on Blue Trisacryl M A. Elution Profile

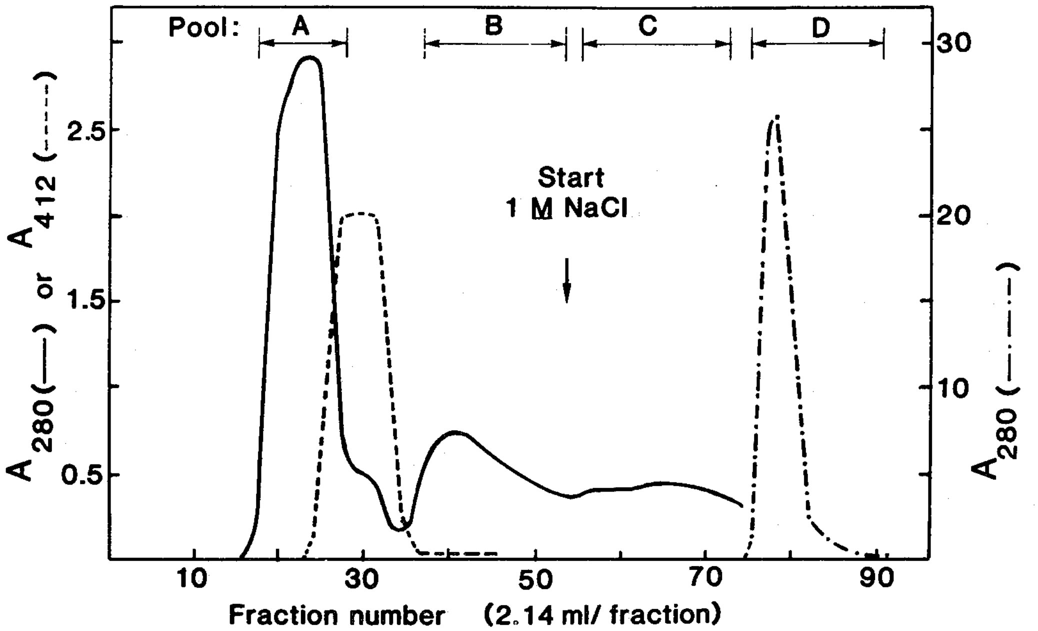

B. Non-reduced 5-12.5% Gradient SDS-PAGE of Chromatographic Pools from the Purification of RTA-IgG Immunoconjugate

| lane | sample | |
|---|---|---|
| 1. | MW standards | |
| 2. | IgG | |
| 3. | derivatized IgG | |
| 4. | RTA | |
| 5. | Pool A | Blue Trisacryl M |
| 6. | Pool B | |
| 7. | Pool C | |
| 8. | Pool D | |
| 9. | Pool A | Ultrogel AcA 44 |
| 10. | Pool D | |
| 11. | Pool C | |
| 12. | Pool B | |

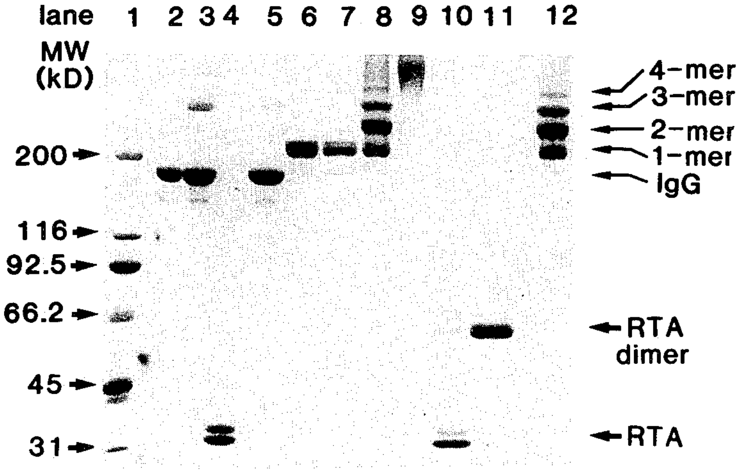

Fractionation of RTA-Containing Components of an RTA-IgG Conjugation on Ultrogel AcA 44

For identification of the pools by SDS-PAGE, see Figure 4-B.

FIG. 6
Salt-Gradient Fractionation of RTA-IgG Immunoconjugate Species on Blue Trisacryl M
A. Elution Profile
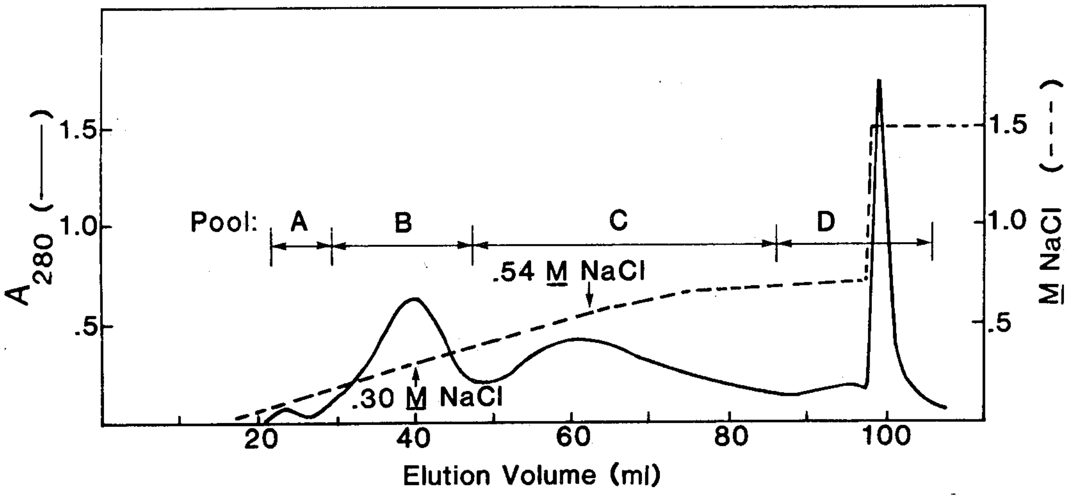
B. Non-reduced 5-12.5% Gradient SDS-PAGE of Chromatographic Pools
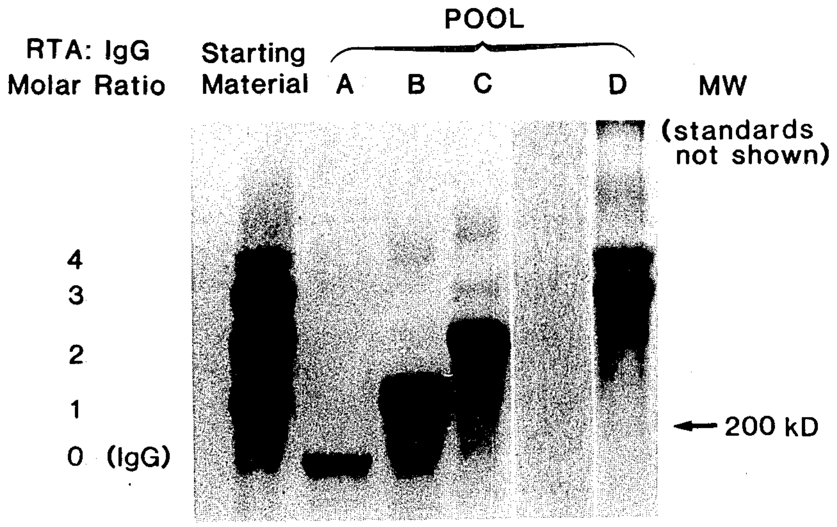

FIG. 7
Salt-Gradient Fractionation of Ricin E1-IgG Immunoconjugate Species on Blue Trisacryl M
A Elution Profile
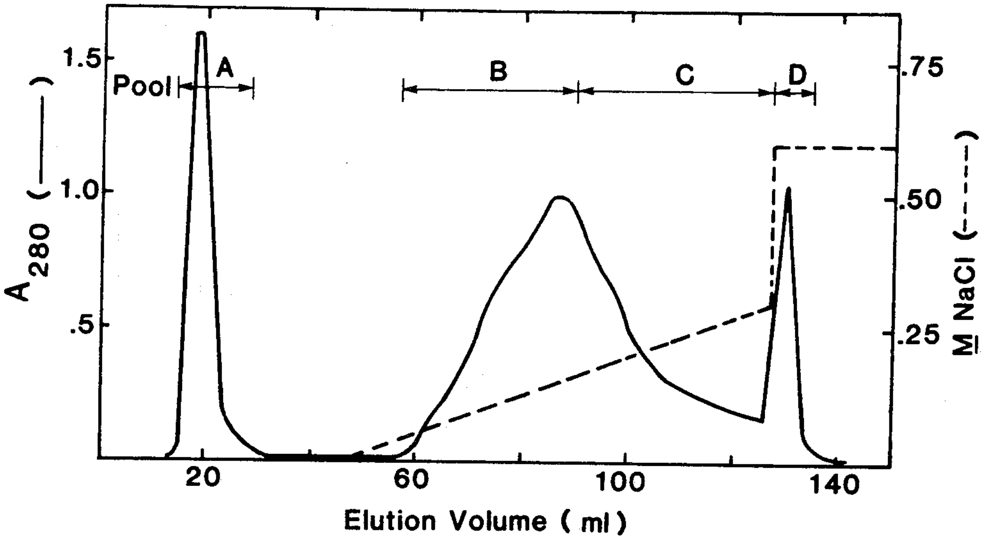
B. Non-reduced 6% SDS-PAGE of Chromatographic Pools
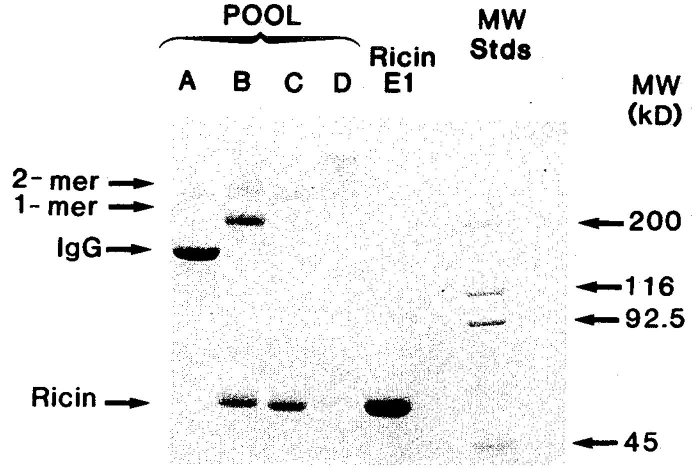

Fractionation on Blue Trisacryl M of Components of Conjugations of IgG with Momordin and Saponarin FIG. 9
Lactose Gradient Fractionation of Castor Bean Extract on Acid-Treated Sepharose CL-4B
buffer: 0.10M Na phosphate, pH8.0
A. Elution Profile
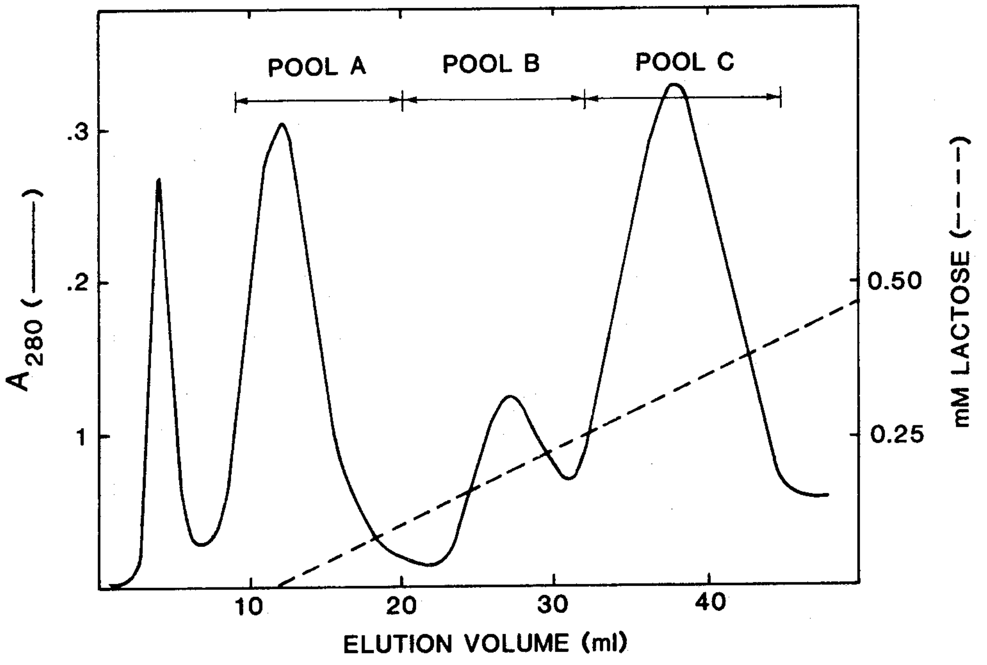
B. Isoelectric Focusing of Chromatographic Pools
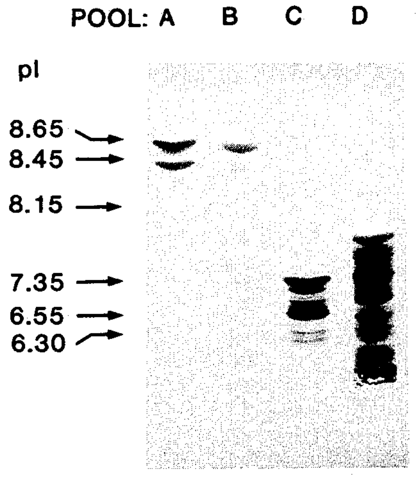

Isoelectric Focusing of Ricin Isotoxins and Their Component Chains

FIG. 11
SDS-PAGE of Ricin Isotoxins and Their Component Chains
A. Isotoxins
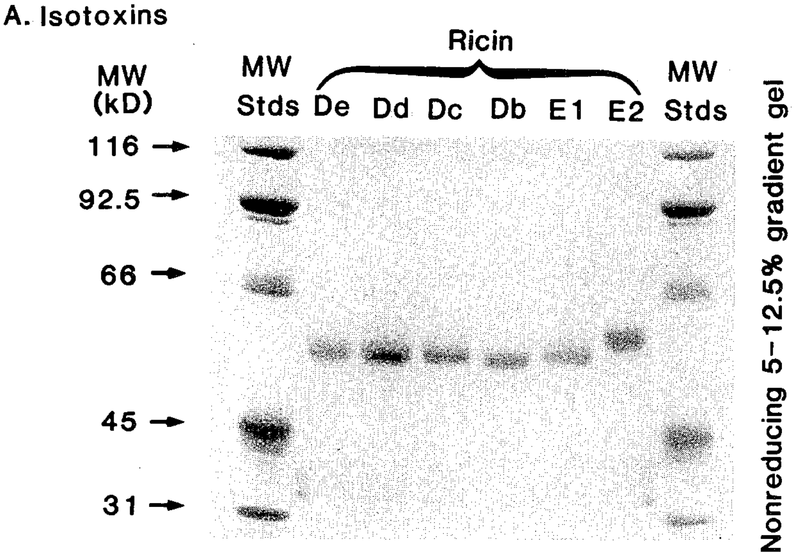
B. Chains
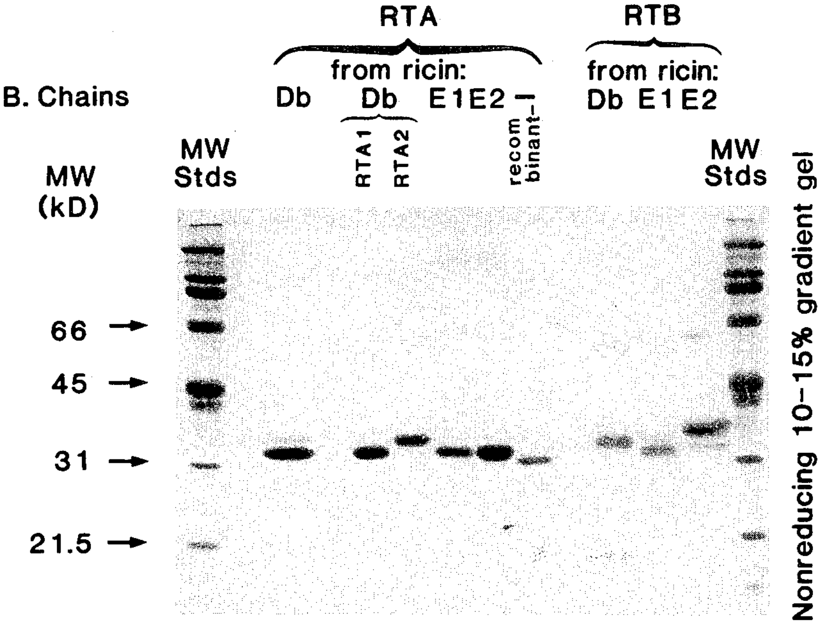

RIBOTOXIN CONJUGATES

This a division, of application Ser. No. 747,114 filed June 20, 1985, now abandoned.

TECHNICAL FIELD

The invention relates to protein purification, specifically with respect to ribotoxins. More particularly, the invention concerns methods using chromatography on immobilized Procion dyes to purify ribotoxin components, to purify ribotoxins and their isotoxins, and to purify ribotoxin conjugates. Also included in the invention are a novel ricin isotoxin and its conjugates.

BACKGROUND ART

Many bacteria and higher plants produce cytotoxic proteins collectively called ribotoxins which function by being taken up by, and then inactivating the ribosomes of a target cell. The ribotoxins are considered to fall into two major classes: NAD+-dependent ribotoxins, which appear to disable ribosomes by covalently attaching ADP-ribose to "elongation factor-2" protein, and NAD+-independent ribotoxins, which appear to inactivate the 60S ribosomal subunit. It is the NAD+-independent ribotoxins and their derivatives to which the separation and purification methods of the invention apply. These ribotoxins affect only eucaryotic ribosomes and because they function enzymatically, they are lethal at low concentrations.

Some of the ribotoxins with which the invention is concerned can be isolated as covalently linked heterodimers consisting of an enzymatically active (ribotoxic) A chain polypeptide linked through a disulfide bond to an enzymatically inactive B chain polypeptide which is responsible for binding to the target cell surface, and which may also facilitate uptake of the cytotoxic portion. Representative heterodimeric ribotoxins which are subject to the methods of the invention are ricin, abrin, and modeccin.

Other ribotoxins are single polypeptides which are cytoloxioally active, and are thus sometimes referred to as "A chain toxins" or "hemitoxins". Examples of such A chain toxins to which the method of the invention is applicable are pokeweed antiviral protein (PAP), mitogillin, restrictosin, momordin, saponarin, and gelonin.

Several ribotoxins, such as ricin, abrin, and PAP, occur in nature in more than one form. Thus, these ribotoxins can be considered to represent several isotoxins—i.e. structurally similar proteins with quantitatively differing functional properties.

Recent reviews of ribotoxins in general include Olsnes, et al, *Molecular Action of Toxins and Virus,* Cohen, et al, ed (1982) El sevier, N.Y. pp 51–105; and Barbieri, et al, *Cancer Surveys* (1982) 1:488–520.

Some attempts have been made to take advantage of the cytotoxic properties of the ribotoxins by employing the unmodified polypeptides as therapeutic agents (see, for example, Fodstad et al, *Cancer Research* (1984) 44:862–862). However most efforts to use ribotoxins therapeutically have been focused on hybrid toxins, in which the cytotoxic moiety is covalently coupled to a "binding moiety" expected to bind specifically to certain cells, virus, or other macromolecules. The most common examples of hybrid toxins are immunotoxins, wherein the cytotoxic polypeptide is conjugated to a specific antibody; however, a variety of other binding moieties may be used.

Many examples of the utility of such hybrid toxins are available. In the simplest concept, an antibody is chosen to recognize an antigen characteristic of an undesired target cell such as a cancer cell. The antibody seeks out the target cell and permits the toxin to kill it. In slightly more complex applications, a conjugate between the toxic polypeptide and an antigen recognized by autoimmune lymphocytes responsible for destroying normal tissue is administered to patients with autoimmune diseases. Hybrid toxins may also be used to aid in preventing transplant rejection either by destroying the lymphocyte cells attacking the foreign material, or by eliminating undesirable cells, accompanying the transplant, which attack host cells.

The hybrid toxins are prepared by covalent chemical coupling of a purified ribotoxin to a binding moiety and purification of the resulting conjugate by separation from unconjugated components. The ribotoxin component may itself need to be generated by reduction of a heterodimeric ribotoxin and separation of the resulting A and B chains from the unreacted heterodimer. The methods of purification provided by the invention are useful in obtaining pure whole ribotoxin, in obtaining pure ribotoxin A chain from heterodimer and in purifying the hybrid toxins from the conjugation mixture.

Hybrid toxin preparation and therapeutic effect have been reviewed by Thorpe, et al, *Immunol Revs* (1982) 62:119–157 and by Edwards, *Pharm Ther* (1983) 23:147–177. Ricin, abrin, their purified A chains, PAP, gelonin, and diphtheria toxin A chain have, for example, all been employed in hybrid toxin preparation and use. When, as usually is the case, hybrid toxins include only the A chains of heterodimeric ribotoxins in order to minimize non-specific binding, the putative advantageous property of the B chains to mediate translocation of the cytotoxic portion into the cell is lost. Optimization of hybrid toxin performance may be possible by selecting whole toxins for conjugation which have desirable intrinsic binding specificities.

Purification steps are critical in preparing any material for therapeutic use. In the particular case of ribotoxin hybrid toxins the preparation just not only be free of impurities from original extracts, but also from unreacted components and side products of the conjugation reaction, and specifically from unwanted B chain moieties derived from a heterodimer. In some applications, homogeneity with respect to the stoichiometric ratio of cytotoxin to binding moiety ratio (i.e. the multilicity) may be beneficial. Generally, conjugation procedures result in mixtures wherein the antibody, for example, is conjugated to 1, 2, 3, or more cytotoxic moieties. Such heterogeneity may complicate the interpretation of results obtained with the preparation, and may affect the therapeutic value as well.

In addition effective purification of the ribotoxin moiety prior to conjugation is more important than it might at first appear. For example, the additional oligosaccharide chain on RTA2 (one of two isoenzyme A chains derived from ricin; see below) may be recognized by the mannose/N-acetylglucosamine clearance system (Stahl, et al, *Proc Natl Acad Sci* (*U.S.A.*) (1978) 75:1399–1403; Kawasaki, et al, *Biochem Biophys Res Commun* (1978) 81:1018–1024). Therefore, conjugates formed with RTA2 may be cleared from circulation more quickly than those formed with the other isoenzyme, RTA1; if so, therapeutic efficacy may be reduced. Ideal hybrid toxins would be formed from purified RTA1 which is, putatively, less rapidly cleared from the blood.

The invention herein provides a successful method to obtain homogeneous preparations of hybrid toxins. It permits separation of hybrid toxins of varying stoichiometry, and also permits separation of isotoxins both of full heterodimeric polypeptides and of ribotoxin A chain. In addition the invention provides a useful method for purifying ribotoxins from their natural sources.

By application of the method of the invention, a previously unknown isotoxin ricin E2, which has unique properties differing from those of the previously known ricin D and ricin E, has been isolated and characterized. Ricin E2 has cytotoxicity levels and binding specificities which result in hybrid toxin derivatives having superior ratios of target-specific cytotoxcity to whole-animal toxicity as compared to corresponding RTA hybrid toxins.

DISCLOSURE OF THE INVENTION

By taking advantage of the peculiar affinity of Procion dye for NAD+-independent ribotoxins for the A polypeptides thereof, for hybrid toxins of the ribotoxins and the A polypeptides thereof, and for at least some of the B polypeptides thereof, methods have been devised which permit a series of separation and purification procedures vital to the preparation of useful therapeutic materials involving these toxins and their components. These methods permit separation of the various NAD+-independent ribotoxin derived materials, which components are useful in the preparation of therapeutic agents. The methods also permit purification of the therapeutic end product.

Thus, in its broadest aspect the invention is related to a method for separating components of a mixture or purifying a desired component from a mixture containing at least one of an NAD+-independent ribotoxin, the A polypeptide of an NAD+-independent ribotoxin, the B polypeptide thereof, or a related hybrid toxin. The hybrid toxin is a conjugate of a cell-binding molecule (most commonly an immunoglobulln or fragment thereof, or a suitable antigen) with the ribotoxin or a ribotoxin A polypeptide. The method comprises treating the mixture with a Procion dye attached to a solid phase support, under conditions wherein at least one of the ribotoxin related components is adsorbed, separating the solid phase from the remainder of the mixture, and then eluting the adsorbed components.

Particular aspects of this general method to which the invention is directed are:

- separation of two or more related NAD+-independent ribotoxins;
- separation of two or more related NAD+-independent ribotoxin A polypeptides;
- separation of the components of a mixture containing an NAD+-independent ribotoxin and its A and B polypeptides;
- separation of the components of a mixture containing hybrid toxins of a ribotoxin or ribotoxin A polypeptide of varying multiplicities with respect to the toxic moiety; and
- separation of ribotoxins. ribotoxin components, or hybrid toxins from unrelated impurities.

In additional aspects, the invention is directed to previously uncharacterized isotoxins, ricins E1 and E2, and to their hybrid toxins.

BRIEF DESCRIPTION OF THE DRAWINGS

FIGS. 1A and 1B are the elution profile and analysis by reduced sodium dodecyl sulfate polyacrylamide gel electrophoresis (SDS-PAGE) of the eluate from Blue Trisacryl M chromatography resolving RTA1 and RTA2.

FIGS. 3A and 3B show the elution profile and isoelectric focusing patterns of the eluate from Blue Trisacryl M chromatography resolving RTA and RTB.

FIGS. 4A and 4B show the elution profile and SDS-PAGE analysis of eluate from Blue Trisacryl M chromatography resolving RTA and RTA immunoconjugate from free IgG.

FIGS. 6A and 6B show the elution profile and nonreduced SDS-PAGE analysis of eluate from Blue Trisacryl M chromatography resolving immunoconjugates of various multiplicities of RTA.

FIGS. 7A and 7B show the elution profile and nonreduced SDS-PAGE analysis of eluate from Blue Trisacryl M chromatography resolving ricin E1, IgG, and ricin E1 immunoconjugates.

FIGS. 9A and 9B show the elution profile and isoelectric focusing patterns of eluate from agarose affinity chromatography resolving ricin D, ricin E1, ricin E2, and castor bean agglutinin.

FIG. 11 shows the comparative molecular weights of the ricin isotoxins and components of FIG. 10 as determined by SDS-PAGE

MODES OF CARRYING OUT THE INVENTION

A. Definitions

Figure 2:
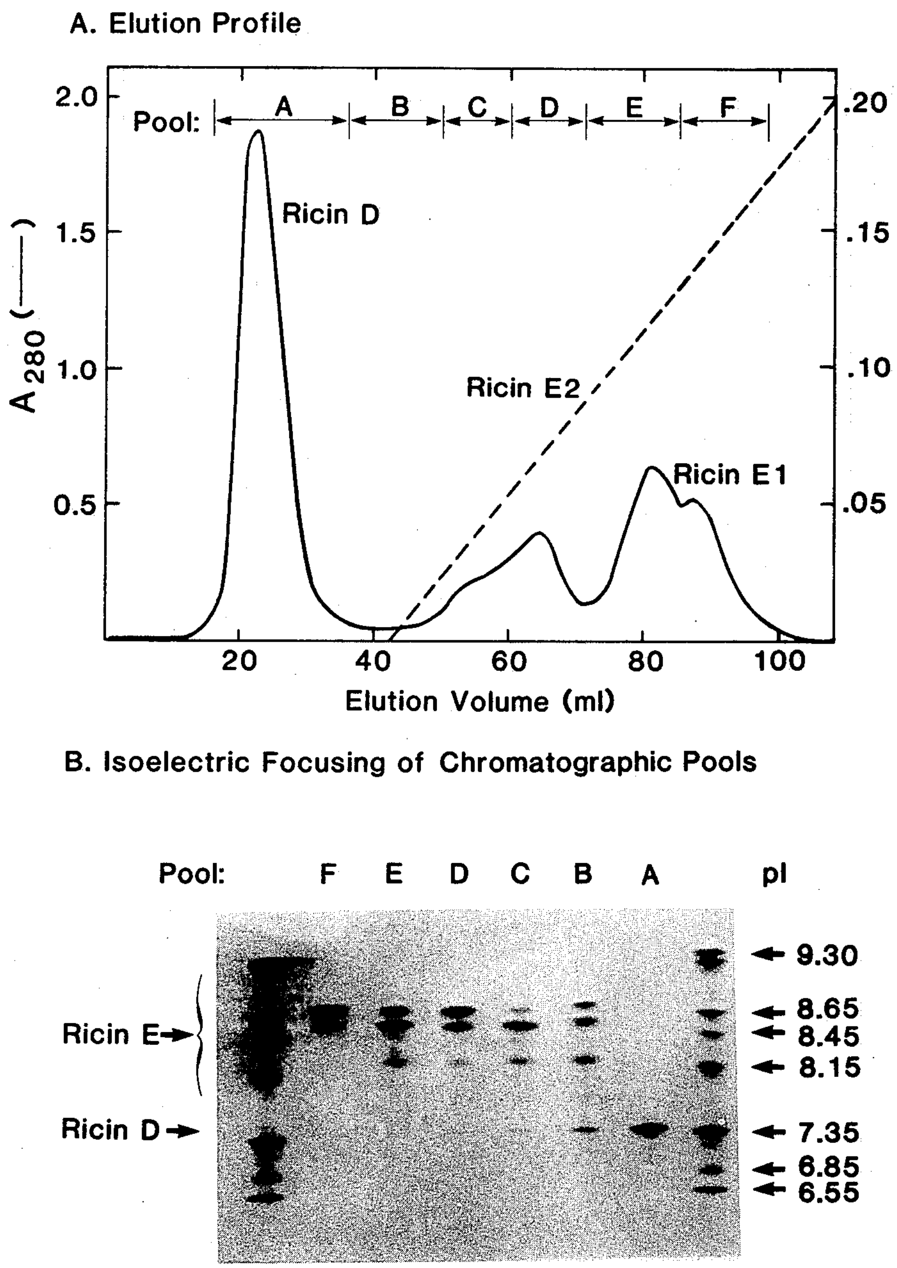
FIGS. 2A and 2B show the elution profile and analysis by isoelectric focusing of the eluate from Blue Trisacryl M chromatography resolving ricin isotoxins D, E1 and E2.

As used herein, "NAD+- independent ribotoxin" refers to a cytotoxic protein which kills eucaryotic cells by catalytically inactivating ribosomes, but which does not require NAD+for its activity. The ribotoxin may contain two polypolypeptides coupled by a disulfide linkage, as is the case for ricin, abrin, or modeccin or may be a single polypolypeptide as, for example, is the case for momordin, gelonin, saponarin, or pokeweed antiviral protein (PAP).

"Ribotoxin A chain or polypeptide" refers to the enzymatically active, cytotoxic component of the above defined NAD+-independent ribotoxins. The ribotoxin A polypeptide may normally function as part of a heterodimer, as in the case of ricin, abrin, or modeccin or may stand alone as an intact ribotoxin as is the case with momordin, gelonin, saponarin, or PAP.

"Ribotoxin B chain or polypeptide" refers to a polypeptide associated with the enzymatically active cytotoxic polypeptide in the case of the heterodimeric ribotoxins, which B polypeptide does not have the cytotoxic or enzymic activity associated with the toxin. These polypeptides are generally responsible for binding the whole toxin to the cells to be attacted. They are attracted to the oligosaccharides at the cell surface and may thus be described as lectins. As explained above, such B polypeptides are present in, for example, ricin, abrin, and modeccin.

Some of the NAD+- independent ribotoxins exist as "isotoxins." These are structurally different forms of the ribotoxin derived from the same organism. A significant example of such isotoxins ar e ricin D and ricin E, both of which derive from castor beans, but which have differing properties with respect to, for example, crystallization characteristics, pI values, and binding specificity and affinity. An additional example is provided by the invention herein—ricins E1 and E2 differ in toxicity and affinity characteristics as a result of unknown differences in B chain structure.

In addition the cytotoxic A chains may also exist as "isoenzymes" which, while exhibiting the same enzymatic activity, and while being derived from the same source, show different adsorption affinities, apparent molecular weights and carbohydrate contents. RTA1 and RTA2 are exemplified herein.

It is recognized that all of the above proteins may exist in a variety of forms relating to state of ionization, glycosylation, binding to other moieties, or minor amino acid substitutions, deletions, or augmentations and the like. In general, the foregoing definitions are intended to include both the ribotoxins and their components as isolated from natural sources, and those with alterations in, for example, state of ionization, glycosylation, amino acid sequence, or 3-dimensional structure. The foregoing modifications may result from chemical or genetic modification, including mutations. The resulting modified polypeptides remain within the definitions so long as they retain some level of native ribotoxicity or native cell-binding capacity or are immunologically cross reactive with the naturally occurring polypeptides.

"Hybrid toxin" refers to a substance which comprises a binding moiety covalently linked with a ribotoxin. The "binding moiety" may be an antibody, antigen, metal transport protein, lipoprotein, nucleic acid, or other molecule which directly or indirectly effects the uptake of the ribotoxin by a target cell. Binding moieties may also include, for example, hormones (Oeltmann et al, *J Biol Chem* (1979) 254:1029–1032), lectins (Uchida et al, *J Biol Chem* (1978) 253:6307–6310). and oligosaccharides (Youle, et al. *Cell* (1981) 23:551–559). Immunoconjugates are the most commonly encountered forms of hybrid toxins, in this case, an immunoglobulin or fragment thereof is used as a binding moiety to secure selective attachment to a target cell or molecule. Hybrid toxins may have varying "multiplicities"—i.e. they may contain one, two, or more ribotoxins or ribotoxin A chains per molecule of binding moiety.

"Procion dye" is used in its conventional sense, and refers to a group of synthetic dyes which are produced principally by Imperial Chemical Industries (ICI) which coined the term Procion, and Ciba Geigy which, for the same class of compounds, uses the term Cibacron. The dyes themselves are sulfonated aromatic chromophores conjugated to cyanuric acid (trichlorotriazine). The Procion dyes are formed by nucleophilic substitution at the chloro substituents of the trichlorotriazine, and the resulting dyes will contain one or two remaining chloro substituents so as, themselves, to be monochloro- or dichlorotriazines. Commercially available dyes, sold under various trade names, include Cibacron Blue F3GA, which is a monochlorotriazine, although some commercial preparations may be a mixture of monochlorotriazine and dichlorotriazine and Procion Red HE3B. Representative structures of their conjugates to a hydroxyl containing immobilization support may be found in Fulton, *Dye-Ligand Chromatography* (1980), Amicon Corp. Lexington Mass., p C.2.

In removing an adsorbed material from a solid adsorbant, an elution "gradient" refers to application to the adsorbant of a substance capable of displacing the adsorbed material in monototically increasing concentration. The displacing substance may operate by affinity, for the adsorbed material or for the adsorbant. Typical substances used to elute adsorbed proteins from Procion dye adsorbants include salts, chaotropic agents, specific immunoglobulins, or, in the case of agarose supports, sugars such as galactose. The choice of eluant will depend on the protein adsorbed and the nature of the support. The concentration gradient applied may be stepwise or continuous.

B. General Methods and Materials

B.1. Ricin Ribotoxins, their Component Polypeptides, and their Hybrid Toxins Ricin provides a convenient model used in the examples below to illustrate the invention as it applies to separation of ribotoxin components, isotoxins, and purification of hybrid toxins. Ricin and a structurally related tetrameric protein, agglutinin, are cytotoxic galactose-binding proteins obtainable in high yield from aqueous extracts of the castor bean. Previous methods of purification include gel filtration chromatography, ion exchange chromatography, and affinity chromatography on agarose, a galactose-rich polysaccharide. (Olsnes, et al., *Biochemistry* (1973) 12:3121–3126; Nicolson, et al, ibid (1974) 13:196–204; Ishiguro, et al. *Toxicon* (1976) 14:157–165; Mise, et al, *Agric Biol Chem* (1977) 41:2041–2046; Cawley, et al, *Arch Biochem Biophys* (1978) 190:744–755; Lin, et al, *Eur J Biochem* (1980) 105:453–459, Genaud, et al, *J Immunol Meth* (1982) 49:323–332.)

Ricin can be cleaved into the cytotoxic A chain (RTA) and a galactose specific lectin B chain (RTB) by reduction, using, for example, β-mercaptoethanol. RTA has a molecular weight of 30.6 kD and pI near 7.8: the most commonly studied form of RTB has a molecular weight of 31.4 kD and a pI near 5.0. The most commonly studied form of ricin has pI near 7.4.

Careful fractionation of castor bean extracts shows the presence of several ricin isotoxins. The distinction between ricins D and E has been previously disclosed (Mise, et al, (supra); Wei, et al. *J Biol Chem* (1978)253:2061–2066: Lin, et al, (supra); Genaud, et al (supra)). Ricin D has a pI near 7.4 and a high affinity for agarose; ricin E has a pI near 8.8 and a low affinity for agarose. There are several reports of purported isotoxins which have been shown (see below) to be more acidic forms of ricin D (Olsnes, et al, *J Biol Chem* (1974) 249:803–810; Ishiguro, et al. Toxicon (1976) 14:157–165; Cawley, et al, (supra)).

The differences in properties between ricins D and E seem to reside in the B chain (Funatsu, et al, *Agric Biol Chem* (1978) 42:851–859). The RTA chains from ricins D and E are identical in composition, pI, and apparent molecular weight. However, ricin D yields two distinct RTA species, RTA1 and RTA2. These isoenzymes differ in molecular weight by SDS-PAGE and in carbohydrate content, and can be resolved by ion exchange chromatography with a very shallow salt gradient (Olsnes, et al, *Biochemistry* (supra)).

The invention herein results in the separation of an additional and previously unreported ricin E isotoxin. For convenience, the ribotoxin most similar to the previous ricin E preparation is designated ricin E1, and the novel ribotoxin is designated ricin E2. Ricin E2 has a pI identical to that of ricin E1. Compared to ricin E1 it is 1% as toxic to mice and 2–4% as toxic to cultured cell lines, is bound to agarose more tightly at moderate to high ionic strength, and is approximately 2 kD larger by SDS-PAGE.

Hybrid toxins, most prominently immunotoxins have been prepared using both RTA and whole ricin. U.S. Pat. No. 4,340,435 discloses the construction of disulfide linked RTA immunotoxins and chromatographic purification of the hybrid toxin. The methods disclosed include agaross affinity chromatography and ion exchange. Ricin and RTA hybrid toxins have also been prepared with alternate binding moieties (Cawley, et al, *Cell* (1980) 22:563–570; Youle, et al, *Cell* (1981) 23:551–559; Morimoto, et al, *J Immunol* (1983) 131:1762–1764). Others have had little difficulty in separating the unconjugated ribotoxin from, for example, the antibody and hybrid toxin by gel filtration due to the large difference in their molecular weights (Thorpe, et al, *Immunol Rev* (1982) 62:119–158; Vitetta, et al, *Proc Natl Acad Sci* (*U.S.A.*) (1983) 80:6332–6335; Thorpe, et al, *Eur J Biochem* (1984) 140:63–71). However, complete removal of unreacted antibody from the immunoconjugate is not usually possible without considerable loss of the conjugate because of their similarity in molecular weight. Until the present invention, there has been no general method for such separations. Furthermore, previously disclosed methods fail to separate efficiently immunoconjugates or other hybrid toxins of various multiplicities which are generally present in the reaction mixtures.

B. 2. Other NAD+-Independent Ribotoxins and Their Hybrid Toxins

Additional NAD+-independent ribotoxins to which the invention is applicable include saponarin which is a single polypeptide ribotoxin purified from *Saponaria officinalis* (soapwort) seeds (Stirpe, et al, *Biochem J* (1983) 216:617–625). It has a molecular weight of 29 kD and pI above 9.5. Momordin, also a single polypeptide ribotoxin is purified from *Momordica charantia* (bitter pear melon) seeds and has a molecular weight of approximately 31 kD and a pI value of approximately 8.6 (Falasca, et al, *Biochem J* (1982) 207:505–509). Pokeweed antiviral protein (PAP) is a single polypeptide ribotoxin purified from *Phytolacca americana* (pokeweed). There are at least three PAP isotoxins with apparent MW 29–30 kD and pI values 8.1–8.5 (Irvin, et al, *Arch Biochem Biophys* (1980) 200:418–425; Barbieri, et al, *Biochem J* (1982) 203:55–59). Abrin is a galactose binding heterodimeric ribotoxin purified from *Abrus precatorius* seeds (jequirty bean). It has a molecular weight of approximately 65 kD, and the natural extract includes several isotoxins which vary in lectin properties and toxicity (Lin et al. *Toxicon* (1981)19:41–51). Abrin is closely related to ricin. The two toxins have similar molecular weights, quaternary structures, lectin specificities, and modes of action (Olsnes, et al *Molecular Action of Toxins and Virus* (supra)). Immunoconjugates have also been prepared using PAP and abrin A chain (Masuho, et al, *Biochem Biophys Res Comm* (1982) 105:462–469; Ramakrishnan, et al, *Cancer Res* (1984) 44:201–208; Hwang, et al, *Cancer Res*, in press).

B.3. Procion Dye Purifications

The sulfonated aromatic moieties of Procion dyes (defined above) are effective affinity ligands for many but not all proteins. The efficacy of interaction is not completely predictable and must be explored on a case-by-case basis; however, members of certain classes of proteins, such as kinases and NAD+or NADP+dependent dehydrogenases, predictably bind to Procion dyes because of structural similarity of the dyes to the coenzymes.

The methods employed in utilizing Procion dye affinity include those generally practiced in the art. For example, a typical procedure is to couple a reactive Procion dye covalently to a polymeric matrix, such as, for example, dextran, acrylic polymers, agarose, or other polymer bearing a hydroxyl or amino group either directly or via a spacer arm. The mixture of proteins is then applied to a column of the derivatized matrix. Under these conditions, some proteins bind to the column; after washing to remove non-adsorbed proteins, the adsorbed proteins are eluted by step-wise or continuous gradient application of salt, polyols, chaotropes, competing affinity reagents, or reagents which bind specifically to the adsorbed protein.

Commercially available Procion dye adsorbants include Affi-gel Blue (Biorad Laboratories) Blue Sepharose Cl-6B and Red Sepharose CL-6B (Pharmacia Fine Chemicals), Dyematrex Gels Blue A, Red A, Orange A, Green A, and Blue B (Amicon Corporation) in addition to Blue Trisacryl M (LKB Instruments). All of the foregoing except Blue Trisacryl M use a cross-linked agarose matrix.

Blue Trisacryl M is Cibacron Blue F3GA (Procion Blue HB) bound to a hydrophilic macroporous acrylic gel. Affinity for one Procion dye is generally predictive of affinity for the others, and Blue Trisacryl M thus serves as a convenient illustration of the general efficacy of the method of the invention. The choice of the optimum dye for affinity chromatography of any particular protein is typically made by screening affinities of the desired materials against representative dyes bound to a support, as is understood in the art.

It should be noted that the nature of the support is not entirely irrelevant. One complication in using agarose based adsorbents with galactose-specific toxins such as ricin and abrin is that the B chain lectin, sites can bind directly to the support. This binding can be prevented by including a competing material such as galactose or lactose in the solvent.

As indicated above, proteins previously shown to be retained on Procion dye affinity columns are the pyridine nucleotide dependent dehydrogenases, kinases, and other adenylate nucleotide and nucleic acid binding proteins, such as RNA and DNA nucleases and polymerases. Procion dye affinity chromatography is also useful for proteins containing hydrophobic domains such as serum albumin, the interferons, and serum lipoproteins. In general, it has been possible to classify proteins into groups which are or which are not adsorbable; the present invention has identified an additional such class—the NAD+-independent ribotoxins. Reviews with regard to Procion dye affinity chromatography are exemplified by Haff, et al, in *Theory and Practice in Affinity Techniques* (1978) Sundaram, et al, eds pp.

23-24, Academic Press, NY; Dean, et al, *J Chromatog* (1979) 165:301-319; and Lowe, et al, *Int J Biochem* (1981) 13:33-40. Immobilized Cibacron Blue F3GA adsorbs diphtheria toxin (Antoni, et al, *Experientia* (1983) 39:881-886). Diphtheria toxin is NAD+-dependent Appukuttan, et al, *Biochim et Biophys Acta* (1979) 580:10-14 report the binding of RTA to soluble Cibacron Blue F3GA based on spectrophotometric evidence, but no effort is made to exploit this interaction for molecular separations. Other disclosures involving use of Procion dyes in protein purification include PCT application No. WO79/00541; EpO application No. 64378 A2; British pat. Nos. GB 2,097,280; and 1,602,432A; French No. 2,353,561; U.S. Pat. No. 4,043,997; British No. 2,053,926; Japanese Kokai No. 82/144005; EPO application No. 27262; German application Nos. DE 3149360A1 and DE 3229132 A1, and East German application No. DD 152,359 Z. None of the foregoing disclosures relate to purification on Procion dyes of ribotoxins which are independent of NAD+or of their hybrid toxins.

B.4. A Novel Ricin Isotoxin

A ricin isotoxin previously known as ricin E has been resolved herein to obtain a novel isotoxin, ricin E2, having different properties from those exhibited and disclosed in the literature for ricin E. The majority ricin isotoxin of "the" isotoxin ricin E, a ricin isotoxin which has substantially similar properties to those previously disclosed for ricin E, has been designated herein ricin E1. The minority component, ricin E2, has binding and cytotoxicity properties which make it a useful addition to the repertoire of available ribotoxins. These properties are set forth in detail in Examples 9 and 10 hereinbelow. Ricin E2 has a different binding affinity pattern than that of either ricin D or ricin E1. It has a lower affinity for agarose than ricin D, but higher than ricin E1. It has a lower affinity for Cibacron Blue than ricin E1, but higher than ricin D. Accordingly, ricin E2 may exhibit a low degree of nonspecific binding when used in a hybrid toxin. Its cytotoxicity, when administered alone, is substantially less than that of either of the previously known ricins. Its immunoconjugates appear also to be less toxic to target cells than corresponding immunoconjugates with ricin E1. (See Example 10 below.) However the ratio of specific to nonspecific cytotoxicity is improved.

An extensive literature exists on whole-ricin hybrid toxins which are conjugates of ricin D (Moolten et al, *Ann N.Y. Acad Sci* (1976) 277:690-699; Youle et al, *Proc Nat Acad Sci* (U.S.A.) (1979) 76:5559-5562; Youle et al. *Proc Nat Acad Sci* (U.S.A.) (1980) 77:5483-5486; Youle et al, *Cell* (1981) 23:551-559; Youle and Neville, *J Biol Chem* (1982) 257:1598-1601; Vallera et al. *J Exp Med* (1982) 155:949-954; Thorpe et al, *Nature* (1982) 297:594-596; Thorpe et al, *Eur J Biochem* (1984) 140:63-71; Weil-Hellman et al, *Cancer Res* (1985) 45:1328-1336). As mentioned above, whole-ricin toxins may be desirable due to the putative translocating properties of RTB. The need to block the normal lectin function of the ricin B chain in order to obtain acceptable selectivity is, however, well established. Co-administration of high concentrations of galactose or lactose (reversible blocking) and chemical modification directed to the lectin site (semi-reversible or irreversible blocking) have been used to overcome the problem of nonspecific binding. The ricin E2 of the invention, however, intrinsically minimizes this problem by virtue of its inherently diminished lectin affinity.

C. Examples

The following examples are intended to illustrate, but not to limit, the invention.

Preparation A

Purification of Ricin and its Component Chains from Castor Beans

The starting materials for Examples 1-6 and 9-11 below were prepared as follows. All steps, except dialysis and protein storage at 3°-6° C. were performed at 20°-25° C. unless otherwise noted. A general scheme for this purification is shown below (parentheses indicate minor components):

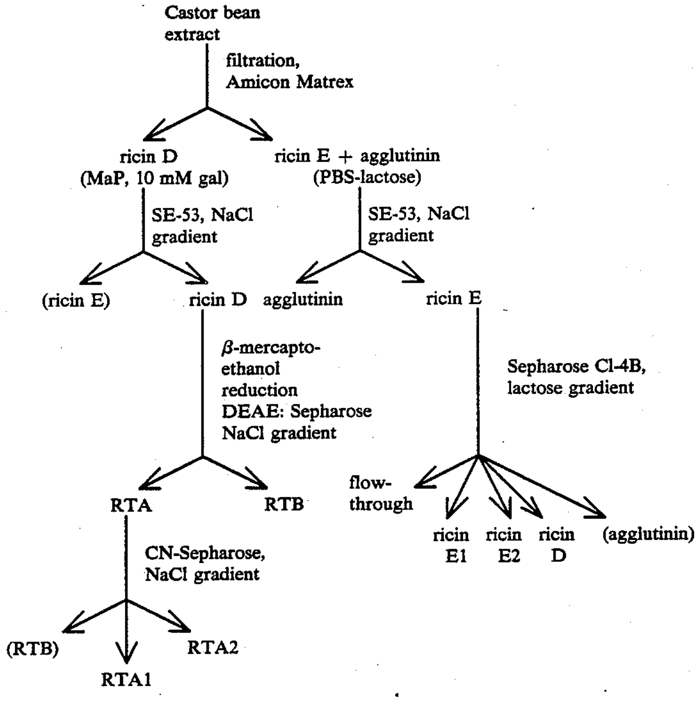

Five hundred g of whole castor beans (*Ricinus communis* var. *sanquineus*) were blended in 1900 ml water. 500 crushed ice, and 100 ml of glacial acetic acid with protection against dispersal of the highly toxic spray. After overnight settling, the extract was passed through a gauze milk filter and a Whatman GF/B filter, adjusted to pH 6.0 with 50% NaOH, and passed through a Gelman 0.2 micrometer filter capsule. The extract was applied to a 13 liter column of Matrex gel (Amicon Corporation) which had been poured in 700 mM Na acetate, pH 5.0, to adsorb the ricin and alglutinin. The column was washed with 12 liters 10 mM Na phosphate, pH 6.1. and then eluted stepwise with 20 liters 10 mM Na phosphate. 10 mM galactose, pH 6.1 which removes ricin D somewhat contaminated with ricin E, and then with 12 liters 10 mM Na phosphate, pH 7.4, 0.1M NaCl, 0.18M lactose (PBS-lactose) to elute the ricin E and agglutinin.

The ricin D-containing fractions were brought to a protein concentration of 4 mg/ml by ultrafiltration (Amicon YM10 membrane) and applied to a 500 ml column of sulfoethylcellulose (Whatman SE-53) pre-equilibrated in 10 mM Na phosphate pH 6 1. The column was eluted with a 3.5 liter linear gradient of 10–50 mM NaCl in the same buffer to obtain the major peak at a conductivity of 3–4 mS as pure ricin D. (The contaminating ricin E may be eluted by stepwise application of 125 mM NaCl in the same buffer.)

The ricin E-containing fractions from the Matrex gel column were ultrafiltered to 10 mg/ml protein, adjusted to pH 6.1, and diluted with water to the same conductivity as 10 mM NaCl, pH 6.1. 13 g of protein were applied to a 1900 ml column of Whatman SE-53 equilibrated in the same buffer and eluted with a 7 liter linear gradient of 20–100 mM NaCl in 10 mM Na phosphate pH 6.1. The first major peak containing most of the agglutinin, was discarded.

The several ricin E-containing peaks were pooled, ultrafiltered to a protein concentration of 10 mg/ml, dialyzed against 0.1M Na phosphate 1 mM Na EDTA, pH 8.0 (Pi-EDTA), and applied to a 300 ml column of Pharmacia Sepharose CL-4B which had been acid-treated (one hour at 50° C. in 1 M HCl followed by washing with Na phosphate). The column was eluted with a 1 liter linear gradient of 0–1 mM lactose in Pi-EDTA. An initial peak of ricin E1, which is retarded but not retained, was followed by a much smaller peak of ricin E2 at 0.2 mM lactose. (Residual ricin D is eluted at 0.35 mM lactose; agglutinin is removed by stepwise elution with 10 mM lactose.)

A portion of the ricin D preparation from the pooled, SE-53 peak was used to prepare ricin A and B chains. The pooled sections were ultrafiltered to give 6–7 mg/ml protein, and brought to 7.5 mM Tris, 1.0 mM EDTA, 2% mercaptoethanol, adjusted to pH 8.4 and allowed to incubate 90 minutes at 25° C. The reduced ricin solution was loaded onto an 800 ml column of DEAE-Sepharose (Pharmacia) equilibrated with 10 mM Tris HCl, 1 mM EDTA, 2% mercaptoethanol (β-ME), pH. 8.4. The column was washed with Tris-EDTA-βME until the $A_{280}$ dropped to that of buffer. The initial, unretained, peak was RTA, which was further purified using CM-Sepharose (pharmacia) pre-equilibrated with 20 mM Na acetate, 2.5 mM Na-EDTA, 2.0 mM dithiothreitol, pH 5.5. The RTA fractions from the DEAE Sepharose were adjusted to pH 5.5 with acetic acid and diluted to give a conductivity below 5 mS, loaded onto a 500 ml column of CM-Sepharose, and then eluted with a 6 liter 0–200 mM NaCl linear gradient in column buffer to obtain two major protein-containing peaks, not always perfectly resolved, designated RTA1 and RTA2. RTA1 and RTA2 are isoenzymes differing in carbohydrate content.

RTB was eluted from the DEAE Sepharose in 10 mM Tris, 2.5 mM EDTA, 2.5 mM DTT, 2% BME, 100 mM NaCl, pH 8.45.

The procedures of Examples 1–6 were conducted at 20°–25° using an elution flow rate of 7.6 cm/hour, unless otherwise noted.

Example 1

Resolution of RTA1 and RTA2

An 18 ml column of LKB Blue Trisacryl M was pre-equilibrated with Pi-EDTA and loaded with 1.1 ml of a solution containing 9.2 mg/ml RTA, pooled eluate from the CM-Sepharose column of preparation A, which had been dialyzed against Pi-EDTA containing 1 mM dithiothreitol. The column was eluted with an 80 ml 0–1M NaCl linear gradient in Pi-EDTA to give the elution profile shown in FIG. 1A. RTA2 ($MW_{app}$=35.5 kD) was eluted at 0.18 M NaCl; RTA1 ($MW_{app}$=33.1 kD) was eluted at 0.48M NaCl. Isoenzyme identity was verified using reduced SDS-PAGE as shown in FIG. 1B; RTA2 migrates more slowly than RTA1 because of a higher degree of glycosylation. Over 90% of the protein was recovered in the two major RTA1 and RTA2 containing peaks. The isoenzyme molar ratio calculated from the areas of the major peaks in FIG. 1A was identical to that obtained by densitometric scanning of lane 2 of FIG. 1B.

EXAMPLE 2

Resolution of Ricin Isotoxins D. E1, and E2

An 18 ml column of Blue Trisacryl M, pre-equilibrated in 1/5 Pi-EDTA, was loaded with a mixture containing 12.5 mg ricin D, 6.0 mg ricin E2, and 8.0 mg ricin E1 (preparation A) which had been diafiltered (Amicon YM30 at 60 psi, 25° C.) in 1/5 Pi-EDTA and ultrafiltered to 1.3 ml. The column was washed with 25 ml buffer and then eluted with an 80 ml linear gradient of 0–0.25M NaCl in the same buffer. Recovery was over 98%.

The elution profile is shown in FIG. 2A; subforms of ricin E1 and E2 differing in pI are partially resolved. The peaks were identified by separate runs of pure proteins on the same column and by isoelectric focusing as shown in FIG. 2B. The first eluting peak is pure ricin D (pI 7.4) and the remaining peaks are ricin E (pI values 8.7, 8.6, and 8.25). Ricin E1 and ricin E2 were differentiated by their behavior on agarose affinity columns.

(Subjection of crude castor bean extract to this procedure results in co-elution of agglutinin and other proteins with ricin D.)

EXAMPLE 3

Resolution of Ricin A and B Chains

Ricin A and B chains were prepared using ricin E1 in a manner similar to that described in Preparation A. Ricin E1 was ultrafiltered as above to 10 mg/ml, brought to 2% in βME and incubated for 1 hour at 20°–25° C. The mixture was filtered through a Gelman 0.45 μM Acrodisc, desalted on a pharmacia PD10 column preequilibrated with Pi-EDTA and incubated for an hour at 20°–25° C. with 1 mM iodoacetamide to block thiols liberated by reduction. Ten to fifteen mg of the reduced and alkylated ricin mixture were then loaded onto a 20 ml column of Blue Trisacryl M preequilibrated in Pi-EDTA at 5° C.; the column was washed with column buffer at a 5 cm/hour flow rate at 5° C. until the first peak of protein, containing all of the RTB and any unreduced ricin, was eluted. RTA was eluted by stepwise application of 0.6M KCl in column buffer. FIGS. 3A and 3B respectively show the elution profile and isoelectric focusing patterns of the two peaks. Each shows several pI values. The first peak (pool A), which was unretarded, was pure RTB chain, the second (pool B), which was eluted by 0.6M KCl, was pure RTA.

In the following examples which employ mouse monoclonal IgG, the antibreast IgGI 280D11, ATCC HB8487 was employed. Other immunoglobulins suitable for use in the procedures disclosed include, for example, 260F9 (ATCC HB8488); 113F1 (ATCC HB8490) and others disclosed in U.S. Ser. No. 690,750, filed Jan. 11, 1985, assigned to the same assignee, and incorporated herein by reference.

Example 4

Fractionation of a Mixture Containing Ricin A Chain, IgG, and Ricin A IgG Conjugate Ricin A chain, purified as in preparation A, was conjugated to mouse monoclonal IgG using standard procedures employing 2-iminothiolane as linker.

In more detail the IgG was ultrafiltered to 30 mg/ml, dialyzed against Pi-EDTA, incubated for 24 hr at 0° C. with 2.2 molar equivalents of 2-iminothiolane and 1 mM 5,5'-dithiobis(2-nitrobenzoate) (DTNB), and then dialyzed exhaustively with Pi-EDTA. The RTA, stored in Pi-EDTA containing 1 mM dithiothreitol (DTT), was ultrafiltered to 10–12 mg/ml and dialyzed exhaustively against Pi-EDTA. After assay of the concentration of blocked thiols on the derivatized IgG (by adding 1 mM DTT to a small sample and measuring the $\Delta A_{412}$) and the concentration of free thiols on RTA (by adding 1 mM DTNB to a small sample and measuring the $\Delta A_{412}$), the two proteins were mixed at 25° C. at a molar ratio of 1.1–1.2 free thiols on RTA per blocked thiol on IgG.

The reaction mixture was applied to a column of Blue Trisacryl M (LKB Instruments, Inc.), pre-equilibrated in Pi-EDTA, using 0.2 ml resin per mg protein. The column was eluted with Pi-EDTA at a flow rate of 10 cm/hour at room temperature to produce a sharp peak of pure IgG, followed by a shoulder of thionitrobenzoate released in the coupling reaction and a low, broad peak of "1-mer", the immunoconjugate species containing one RTA per IgG molecule. The column was then eluted stepwise with 1M NaCl in Pi-EDTA to obtain a sharp peak containing immunoconjugates of various multiplicities of RTA binding to IgG. The elution profile is shown in FIG. 4A.

Analysis of the eluted protein peaks by SDS-PAGE is shown in FIG. 4B in lanes 5–8; lanes 9–12 represent gel filtration fractions (see below). The unreacted IgG (pool A) was clearly separated from conjugates (pools B-D). The 1-mer was spread through several fractions, but the higher-multiplicity conjugates were not eluted until the 1M NaCl was applied (pool D).

The fractions containing the conjugates and RTA (B, C, and D) were ultrafiltered to 20 mg/ml protein and applied to a column of Ultrogel AcA44 (LKB Instruments, Inc.) scaled to have a sample/bed volume ratio below 0.03 and equilibrated with 0.15M Na phosphate, pH 7.1, at 5° C.

Figure 5:
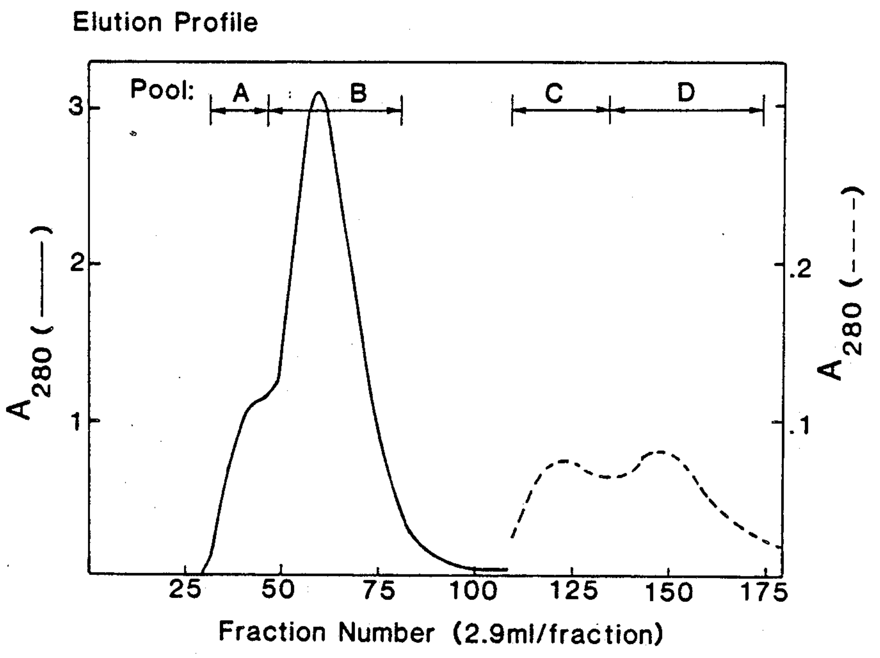
FIG. 5 shows the separation of unconjugated RTA from its immunoconjugates using gel filtration chromatography.

Elution of the column in the same buffer at a flow rate of 6 cm/hr resulted in an elution profile (FIG. 5) comprised of an initial peak containing a mixture of the immunoconjugate species with different RTA multiplicities followed by unconjugated ricin A. Pool B of FIG. 5 was a mixture of immunoconjugate species containing 1–4 RTA molecules/IgG, substantially free of unconjugated IgG and RTA. Pools C and D contained RTA dimer and RTA respectively. The identification of these pools was verified by SDS-PAGE, as shown in FIG. 4B; lane 10 represents pool D, lane 11, pool C, and lane 12, pool B.

Total recovery of protein in the two chromatographic steps was over 90%.

To resolve the immunoconjugates of various multiplicities 19 mg of the immunoconjugate mixture obtained from the AcA44 column (pool B) was applied at a concentration of 5.1 mg/ml in Pi-EDTA to an 18 ml column of Blue Trisacryl M; and the column was then eluted with an 80 ml 0–1 M NaCl linear gradient in Pi-EDTA at a flow rate of 5.9 cm/hr followed by an increment to 1.5M NaCl in the same buffer. FIGS. 6A and 6B show the elution profile and the SDS-PAGE analysis of the peaks. The 1-mer (pool B), which was eluted at 0.3M NaCl and 2-mer (pool C), which was eluted at 0.54M NaCl, were separated from the higher-multiplicity conjugates, (pool D). which were eluted at higher salt concentration, as separate but overlapping peaks.

Example 5

Fractionation of a Mixture Containing Ricin E1, IgG and Ricin E1-IgG Conjugate

The immunoconjugate was prepared as follows:

A sample containing 32 mg ricin E1, 11 mg/ml in Pi-EDTA, was incubated 12 hr at 0° C. with 0.8 molar equivalents of N-succinimidyl 3-(2-pyridyldithio)propionate (SPDP) and 1.5 hr at 25° C. with an additional 1.0 molar equivalent of SPDP. Three molar equivalents of dithiothreitol (DTT) were added, and the derivatized ricin E1 was exhaustively dialyzed against Pi-EDTA and assayed to have 0.63 free thiols per ricin by adding 1 mM DTNB to a small sample and measuring the 412 nm absorbance. Twenty-six mg of mouse monoclonal IgG, 27 mg/ml in Pi-EDTA, were incubated for 11 hr at 0° C. with 1.2 equivalents of 2-iminothiolane and 1 mM DTNB and dialyzed exhaustively against the buffer. Spectral assay of the thionitrobenzoate released during derivatization showed that 0.89 blocked thiols were added per IgG molecule. The two derivatized proteins were then mixed at 25° C. at a molar ratio of 1.2 free ricin E1 thiols/IgG blocked thiol group. The absorbance signal at 412 nm showed that the reaction leveled off at 90% of completion after 1 hour.

The reaction mixture was dialyzed against 1/5 Pi-EDTA and loaded onto a 32 ml Blue Trisacryl M column, washed with 25 ml column buffer, and then eluted with an 80 ml 0–0.3M NaCl linear gradient in the same buffer at 6.8 cm/hr, followed by a step to 0.6M NaCl. FIGS. 7A and 7B are the elution profile and nonreduced 6% SDS-PAGE analysis of the peaks obtained. An initial peak containing unconjugated immunoglobulin (pool A) is followed by a partially resolved immunoconjugate of multiplicities 1 and 2 in admixture with underivatized ricin E1 (pools B and C). However, the pool B fraction contains virtually all of the conjugate of multiplicity 1 and relatively little ricin. The peak eluted by 0.6M NaCl (pool D) is a mixture of higher multiplicity conjugates and very little underivatized ricin. The high MW band in pool A is not conjugate, but dimerized IgG which routinely is formed in low yield during derivatization.

The peak containing conjugate of multiplicity 1 and ricin E1 was further fractionated on Ultrogel AcA34 (LKB Instruments, Inc.) to produce immunoconjugate containing less than 1% ricin E.

Example 6

Fractionatlon of Momordin, IgG, and Momordin IgG Immunoconjugate

Momordin was purified using the method of Barbieri, et al, *Biochem J* (1980) 186:443–452. The momordin was conjugated with IgG using iminothiolane and purified as follows:

24.7 mg of momordin, 2.2 mg/ml in Pi-EDTA, were incubated for 16 hours at 4° C. with 28 molar equivalents of 2-iminothiolane, dialyzed exhaustively against Pi-EDTA, and assayed to have 1.08 free thiols per toxin molecule by adding 1 mM 5.5'-dithiobis(2-nitrobenzoate) (DTNB) to a small sample and measuring the change in $A_{412}$. 47 mg of mouse monoclonal IgG. 31 mg/ml in Pi-EDTA. were incubated for 6 hours with 2.5 equivalents of 2-iminothiolane and 1 mM DTNB, dialyzed exhaustively againt Pi-EDTA and assayed to have 1.93 blocked thiols per IgG by adding 1mM DTNB dithiothreitol to a small sample and measuring the change in $A_{412}$. The two derivatized proteins were mixed at 25° C. àt a molar ratio of 1.2 free thiols on momordin per blocked thiol on IgG. The coupling reaction. monitored spectrophotometrically at 412 nm, was complete in 1 hour.

Figure 8:
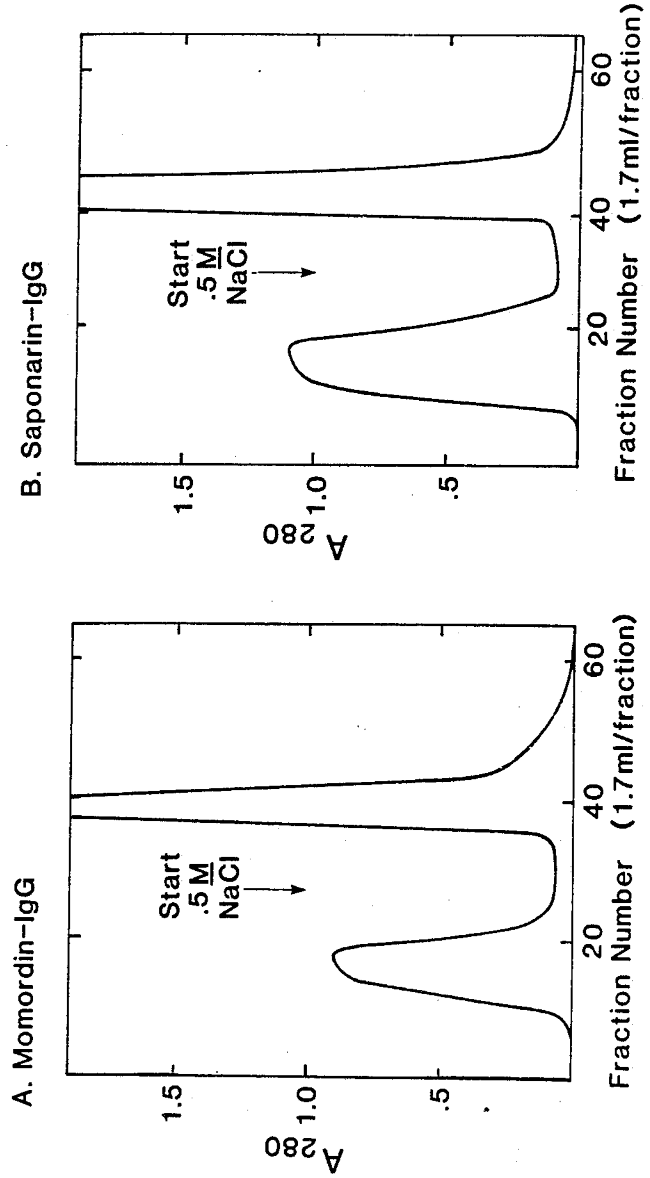
FIGS. 8A and 8B show the elution profiles of Blue Trisacryl M chromatography columns used to separate momordin, its immunoconjugates, and IgG, and to separate saponarin, its immunoconjugates, and IgG.

The reaction mixture was dialyzed against 0.010 M Naphosphate 0.001M Na EDTA, pH 8.0 (low $P_i$-EDTA) and loaded onto Blue Trisacryl M at 0.5 ml bed volume/mg IgG reacted and eluted with low Pi-EDTA until unretarded protein was off the column. The column was then eluted using 0.5M NaCl in the same buffer to obtain the elution profile shown in FIG. 8A. Analysis using nonreduced SDS-PAGE showed that the first peak was IgG and that the seoond contained unreacted toxin plus all of the RTA multiplicities of conjugate.

The mixture containing immunoconjugate was ultrafiltered (Amicon YMIO at 60 psi) t ©a protein concentration of 1–2 mg/ml. dialyzed into 0.15M Na phosphate. 0.5M KCl pH 6.8 and passed over an Ultrogel AcA44 column at 4° C. (sample/bed volume ratio$<$0.02) which completely resolved immunoconjugate from unreacted toxin.

Example 7

Fractionation of Saponarin, IgG, and Saponarin-IgG Conjugates

In a manner analogous to that described in Example 6, con)ugates of saponarin with mouse monoclonal IgG were prepared and separated from remaining unreacted toxin and IgG. When 13 molar equivalents of iminothiolane were incubated with saponarin the derivatized toxin contained 0.89 free thiols per toxin moleoule. The saponarin was purified initially by the method of Stirpe, et al, *Biochem J* (1983) 216:617–625. The Blue Trisacryl M elution profile is shown in FIG. 8B.

Example 8

Fractionation of Pokeweed Antiviral Protein (PAP), IgG, and PAP-IgG Conjugate

PAP was purified from the spring foliage of *Phytolacca americana* by the method of Irvine et al (*Arch Biochem Biophys* (1980) 200:418–425). The purified PAP was conjugated to mouse monoclonal IgGl as follows:

Protein derivatization, coupling and gel filtration were performed in 40 mM Na phosphate, 200 mM NaCL (PBS). IgG (5–10 mg/ml in PBS, pH 7.6) Was incubated at 25° C. for 30 min With a threefold molar excess of SpDp and desalted at 3°–5° C. on a Sephadex G-25 (Pharmacia) column equilibrated in pH 6.5 PBS. PAP (5 mg/ml in pH7.6 PBS) was SPDP-derivatized and desalted in the same manner. The PAP was then ultrafiltered (Amicon YM10 membrane) to a concentration of 5 mg/ml, reduced with 5 mM dithiothreitol. and desalted as above. The concentration of blocked thiols on derivatized and desalted protein was calculated from the $\Delta A_{343}$ after adding dilute DTT. The concentration of free thiols on reduced derivatized protein was calculated from the $\Delta A_{343}$ after adding dilute 2,2'-dithiodipyridine. IgG bearing 1.5–2.3 blocked thiols/-molecule was mixed with a threefold molar excess of PAP bearing 1.6 molecules of free thiol/molecule. The pH was adjusted to 7.6 and the mixture ultrafiltered.

After ultrafiltration on an Amicon YM10 membrane to a final protein concentration of 5–10 mg/ml and dialysis overnight at 3°–5° C. against pH 7.6 PBS, unreacted PAP was removed (rom the mixture by gel filtration on Sephacryl S-300 (pharmacia) at 3°–5° C.: the sample/bed volume ratio was 0.01–0.03.

Pooled fractions containing IgG and conjugate were ultrafiltered (Amicon YM10 membrane) and desalted on a Sephadex G-25 column equilibrated with 10 mM Na phosphate, 1 mM EDTA pH 8.0 at a sample/bed volume ratio of 0.2.

A sample containing 2 mg of protein at a concentration of 1 mg/ml was chromatographed on a 1.4 ml column of Blue Trisacryl M (LKB Instruments) at 25° C. in 10 mM Na phosphate 1 mM EDTA, pH 8.0. After elution of unretarded protein, a second, very sharp, peak was eluted in 1M NaCl to provide an elution profile similar to those shown in FIG. 8. Non-reduced SDS-PAGE showed that the unretarded peak was pure IgG. and the peak eluted at 1M NaCl contained immunoconjugate as a mixture of multiplicities of 1–3. Total recovery of protein from affinity chromatography was 88%.

Example 9

Characterization of Ricins D, E1, and E2

Figure 10:
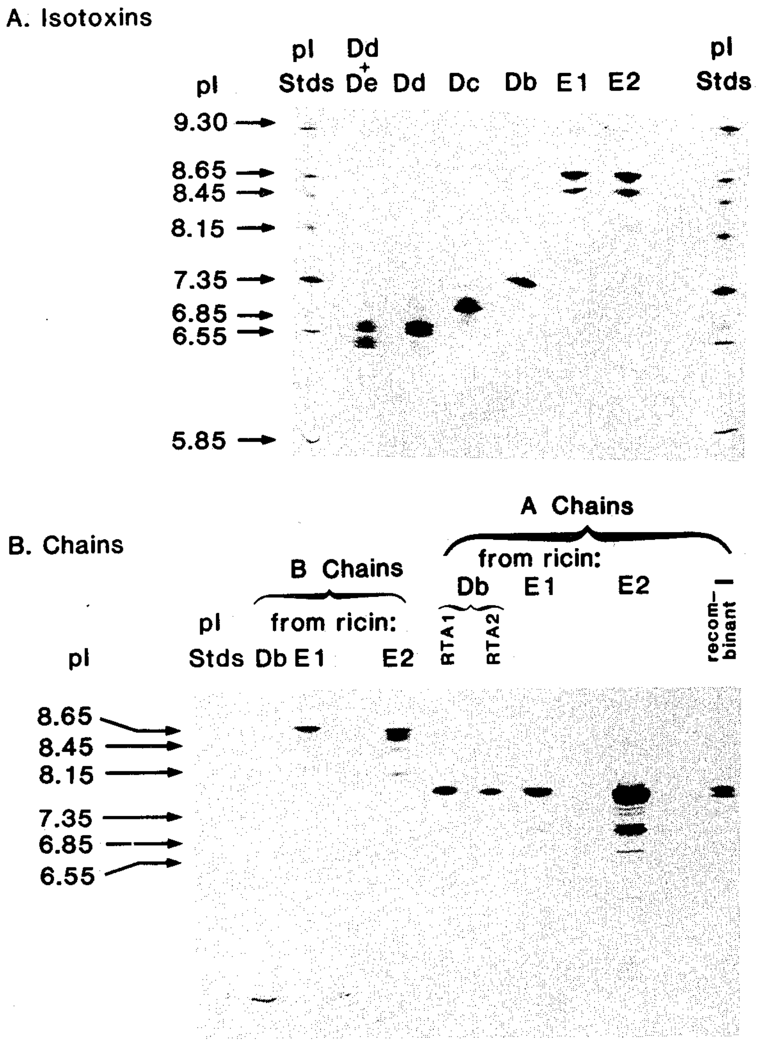
FIGS. 10A and 10B show the isoelectric focusing patterns of ricin isotoxins and their A and B chains.

FIGS. 9, 10, and 11 illustrate the comparative lectin and physical properties of the ricin isotoxins prepared from castor bean.

FIG. 9A shows the elution pattern obtained when a crude extract of castor beans (*Ricinus communis* var *sanquineus*) was applied to a column of acid treated Sepharose CL-4B (pharmacia) and eluted with a shallow lactose gradient. The results of isoelectric focusing performed on the fractions (shown in FIG. 9B) establish that peaks A and B contained ricin E isotoxins identified as ricin E1 and ricin E2 respectively; pool C contained ricin D. The first sharp peak contained non-ricin protein; castor bean agglutinin (pool D in FIG. 9B) was eluted at the end of the gradient by a step to 0.2M lactose. Elution with galactose instead of lactose improved the resolution of ricins E1 and E2 (pools A and B) but destroyed the resolution of ricins E2 and D (pools B and C).

Isoelectric focusing was performed on LKB PAGplates, pH 3.5–9.5, on a LKB model 2117 Multiphor bed cooled to 8°–10° C. following the instructions supplied with PAGplates. As shown in FIG. 9B pools A and B have pI values characteristic of ricin E, pool C contains ricin D. Pool D (not shown in FIG. 9A) contains castor bean agglutinin a galactose-specific lectin showing significant amino acid homology to ricin but which is less toxic.

The separation shown in FIG. 9 provided the basis for the large scale purification of ricins E1 and E2 described in preparation A.

The behavior of ricins D. E1, and E2 on agarose as shown above and on Procion dye columns, as shown in Example 2 demonstrate that these ribotoxins have different lectin activities. Ricin D has the highest affinity for agarose and lowest affinity for Cibacron Blue F3GA; ricin E1 has the highest affinity for Cibacron Blue F3GA and lowest affinity for agarose. (Agarose is a galactose-containing polysaccharide; the Procion dye may be considered to mimic an as yet unidentified cell surface receptor.) Ricin E2 has intermediate affinity for both agarose and Cibacron Blue. (RTA itself has a much higher afffinity for the Procion dye than the heterodimer—compare the elution conditions of Examples 1 and 2. Thus. the binding site of RTA must be masked in the whole isotoxins.)

FIG. 10A shows IEF patterns of highly purified ricins E2, E1, and D from preparation A, including several charge subclasses of ricin D which can be resolved by salt gradient elution of ricin D from sulfoethylcellulose at pH 6.1. Among the ricin D isotoxins, labeled Db-De in otder of decreasing pI. ricin Db is the naturally most abundant form and the one commonly referred to as "ricin D" in the literature. As shown in FIG. 10A ricins E1 and E2 show identical IEF patterns with pI values of 8.7, 8.6 and 8.2. In contrast, all ricin D isotoxins are significantly more acidic; furthermore they show no functional or structural differences apart from their pI values.

FIG. 10B shows IEF patterns for the A and B chains of ricins E2, E1, and Db. Ricin Db B chain has a pI of 5.1 substantially different from the pI values of 8.7, 8.6 and 8.2 for the B chains of ricin E1 and E2. The A chain pI patterns are substantially the same for all three isotoxins; the apparent anomaly in the pattern shown for RTA from ricin E2 is due to overloading of the gel Not only are ricins E1 and E2 identical in pI and the distrihution of charge subclasses, but it is clear that their molecular charge characteristics are determined largely by their B chain structures.

FIG. 11A shows the results of non-reduced SDS-PAGE using ricins E1 and E2 and the various subclasses of ricin D from preparation A. All isotoxins show an approximate molecular weight of 58 kD except for ricin E2, which appears to be heavier by 2 kD.

FIG. 11B shows corresponding results obtained for the A and B chains of ricins E2, E1, and Db. RTA from ricin Db contains two isoenzymes, RTA1 and RTA2. RTA2 is 30% as abundant as RTA1 and is more heavily glycosylated. The effect of glycosylation on apparent molecular weight can be seen by comparing RTA2. RTAI and recombinant RTA, a non-glycosylated species Which has been cloned and expressed in *E. coli* at Cetus Corporation (U.S. patent application No. 715,934, filed Mar. 5, 1985). The A chains from ricins E1 and E2 show identical molecular weights to RTA1. The B chains of ricins Db E1 and E2 have apparent molecular weights of 34 kD. 31.5 kD. and 36 kD respectively. (The minor bands in the RTB lanes are due to slight oxidation to RTB dimer and contamination with trace RTA.)

The results shown in FIG. 11 support the hypothesis that the structural differences among ricins D. E1, and E2 reside in their B chains. The lectin differences between ricins D, E1, and E2 are also consistent with B chain structural differences. The identical IEF behavior of the B chains from ricins E1 and E2 implies that these polypeptides are very similar or identical in amino acid composition.

Example 10

Toxicity of Ricins D, E1, and E2

A. In Vitro Cytotoxicity

Cytotoxicity of ricins D, E1, and E2 was measured using 4 cell lines: MCF7 (human breast tumor, ATCC HTB22); CC95 (human foreskin fibroblast); Vero (green monkey kidney ATCC 81); and L929 (mouse fibroblast, ATCC CCLl). The Vero and L929 lines were cultured on DMEM medium (9% $CO_2$) containing 10% fetal calf serum. 1% L-glutamine. lantibiotic-/antimycotic. MCF7 cells were cultured under identical conditions except for the use of 6fetal calf serum and with the addition of 1% nonessential amino acids and 0.2% insulin. CC95 cells were cultured in RPMI medium (5% $CO_2$) containing 15% fetal calf serum, 1% L-glutamine and 1% antibiotic.

Cytotoxicity was measured as follows: serial dilutions of toxins in 0.01M Na phosphate. 0.10 NaCl, 0.1 mg/ml BSA. pH 7.4 were added to $4\times10^4$ cells in 1 ml volumes of tissue culture medium contained in 8 ml glass scintillation vials. After incubation at 37° C. for 2 hr, the medium was aspirated; then the monolayers were washed with 0.01M Na phosphate, 0 10 NaCl pH 7.4. and incubated for 2 hr at 37° C. in 0.5 ml methionine-free tissue culture medium supplemented with 0 5 $\mu$Ci L-[$^{35}$S]methionine (1400 Ci/mmole).

After aspiration of the labeling medium the cell monolayers were washed twice with 10% trichloroacetic acid containing 1 mg/ml methionine. dried and scintillation counted. The results are reported as toxin concentration inhibiting protein synthesis by 50% ($TCID_{50}$), a value obtained by interpolation of a graph of cpm vs log toxin concentration. $TCID_{50}$ values were obtained with and without the addition of 50 mM lactose, which competes with cell surface oligosaccharides for binding to galactose-specific lectins. The results are shown in Table 1.

TABLE 1

Comparative Cytotoxicities of Ricin Isotoxins Toward Four Cultured Cell Lines

| | MCF7 | CC95 | Vero | L929 |
|---|---|---|---|---|
| **$TCID_{50}$ Values in the Absence of Lactose (nM)** | | | | |
| Isotoxin | | | | |
| Dd | .0001 | .037 | .0006 | .011 |
| Db | .0001 | .026 | .0005 | .014 |
| E1 | .013 | .34 | .007 | .013 |
| E2 | .68 | 11 | .3 | .32 |
| **$TCID_{50}$ Ratios for Pairs of Isotoxins in the Absence of Lactose** | | | | |
| Pair | | | | |
| Db/Dd | 1 | .7 | .8 | 1.3 |
| E1/Db | 130 | 13 | 15 | .9 |
| E2/E1 | 52 | 32 | 40 | 25 |
| E2/Db | 6800 | 420 | 600 | 23 |
| **$TCID_{50}$ Ratio: +/− 50 mM Lactose** | | | | |
| Isotoxin | | | | |
| Dd | 500 | 110 | 1100 | 280 |
| Db | 570 | 150 | 1300 | 250 |

TABLE 1-continued

Comparative Cytotoxicities of Ricin Isotoxins Toward Four Cultured Cell Lines

| | MCF7 | CC95 | Vero | L929 |
|---|---|---|---|---|
| E1 | 6 | 8 | 40 | 23 |
| E2 | 15 | 70 | 230 | 150 |

As shown in Table 1, the two subclasses of ricin D tested show identical cytotoxicities, whereas in E2 is approximately 2-4% as cytotoxic as ricin E1 on all cell lines tested. However, the ratio of cytoxicities of ricin D and E isotoxins varies with cell line used. The relative uniformity of the E2/E1 radio supports the interpretation that ricin E2 has the same lectin specificity as ricin E1 but is much less affine for the ricin E cell-surface receptor. The wide variation of E2/Db ratios suggests that these two lectins target different cell-surface receptors with varying distributions on different cells In addition, ricin D appears the most susceptible to lactose blockade followed by ricin E2 followed by ricin E which order parallels the differences in affinity for agarose as evidenced by the elution pattern in FIG. 9.

B. In Vivo Toxicity

Table 2 shows the $LD_{50}$ values obtained after intraperitoneal injection of serial doubling dilutions of toxin in tissue culture medium into groups of 2-3 18-20 g male BALB/c mice.

TABLE 2

Comparative Toxicities of Ricin Isotoxins Toward Mice

| Isotoxin | $LD_{50}$ ($\mu$g/mouse) 3-day (2 mice/dosage) | 7-day (3 mice/dosage) |
|---|---|---|
| mixed Dc, Dd, De | .19 | — |
| Db | .19 | — |
| E1 | .13-.25 | .045 |
| E2 | — | 7 |

As shown in Table 2 ricins D and E1 show approximately the same toxicity; ricin E2 is less toxic by two orders of magnitude.

Example 11

Characterization of Immunotoxins Using Ricins E1, E2, and RTA

The immunoconjugate of ricin E2 with mouse monoclonal IgGl was prepared in a manner similar to that set forth for ricin E1 immunoconjugate preparation in Example 5. After reaction of ricin E2 with SPDP, reduction of the derivatized ricin reaction of IgG with 2-iminothiolane in DTNB, dialysis of the two derivatized proteins, and mixture at a molar ratio of 1.2 free thiols on ricin E2 per blocked thiol on IgG. the coupling mixture was incubated overnight at 4° C. with 10 mM iodoacetamide and dialyzed against 0.15M Na phosphate, pH 7.1. The reactants and products were then separated on a column of acid-treated Sepharose CL-4B in the following manner. The dialyzed protein was applied to a column of acid-treated Sepharose CL-4B (7 ml bed volume/36 mg protein) washed with the same buffer. It was eluted with 1.5 column volumes of the same buffer, followed by a linear gradient to 1 mM lactose (7 column volumes) and a step to 10 mM lactose all in 0.15M Na phosphate pH 7.1, at 3°-6° C. at a flow rate of 6 cm/hr. A first sharp peak consisted of pure unreacted IgG, followed by 3 peaks containing respectively immunoconjugate of multiplicity 1, unreacted ricin, and immunoconjugate of multiplicities<2. The identities of the peaks were established by non-reduced 5–12.5% gradient SDS-PAGE. Because the immunoconjugate peaks are not completely resolved from the ricin, they were pooled, ultrafiltered to protein concentrations between 5 and 20 mg/ml. and fractionated by gel filtration on a column of LKB Ultrogel AcA 34 in 0.15M Na phosphate, 0.010M lactose pH 7.1 with elution at 3°–6° C., 5 cm/hr with a sample/bed volume ratio of 0.01–0.02. Almost pure conjugate with a multiplicity of 1 and a mixture of conjugate species with multiplicities of 2–4 were obtained free of ricin.

The immunoconjugates of ricin E2 prepared as in the previous paragraph were compared to immunoconjugates of RTA (prepared as described in Example 4) and ricin E1 (prepared as described in Example 5) with respect to cytotoxicity against MCF7 cells and with respect to in vivo toxicity in mice using procedures set forth in Example 10. The results are shown in Table 3.

TABLE 3

| Immunoconjugate | $TCID_{50}$ (minus lactose) on MCF7 (nM) | $LD_{50}$ μg/mouse | $LD_{50}$ pmole/mouse | Picomolar $LD_{50}$ MCF7 $TCID_{50}$ |
|---|---|---|---|---|
| RTA-280D11 | 0.8 | 170 | 810 | 1000 |
| ricin E1-280D11 (multiplicity 1) | 0.002 | .42 | 2.0 | 1000 |
| ricin E2-280D11 (multiplicity 1) | 0.039 | 24 | 110 | 3000 |
| ricin E2-280D11 (multiplicity 2) | 0.009 | 14 | 52 | 6000 |

As shown in Table 3, the ratio of $LD_{50}/TCID_{50}$ is improved for the ricin E2 conjugates; this fact indicates better targeting for the desired tumor cells for these derivatives. In addition, immunoconjugates obtained with all whole ricin forms are considerably more cytotoxic and more toxic in vivo than the corresponding conjugates of RTA. This second property may render whole-ricin-E immunotoxins more economical to make and use than RTA immunoconjugates, because they should be equally effective at much lower doses.

I claim:

1. Ricin E2 conjugated to a binding moiety.

2. The hybrid toxin of claim 1 wherein the binding moiety is an immunoglobulin.

3. The ricin E1 chain in substantially pure form conjugated with a binding moiety.

4. The ricin E1 conjugate of claim 3 wherein the binding moiety is an immunoglobulin.

* * * * *